(12) United States Patent
Epler et al.

(10) Patent No.: US 7,024,370 B2
(45) Date of Patent: Apr. 4, 2006

(54) METHODS AND APPARATUS FOR EARLY DETECTION OF HEALTH-RELATED EVENTS IN A POPULATION

(75) Inventors: John Epler, Evanston, IL (US); Michael J. VanRooyen, Cockeysville, MD (US); Mark D. Crockett, Naperville, IL (US)

(73) Assignee: P) CIS, Inc., Rosemont, IL (US)

( * ) Notice: Subject to any disclaimer, the term of this patent is extended or adjusted under 35 U.S.C. 154(b) by 0 days.

(21) Appl. No.: 10/106,841

(22) Filed: Mar. 26, 2002

(65) Prior Publication Data

US 2003/0187615 A1 Oct. 2, 2003

(51) Int. Cl.
*G06F 159/00* (2006.01)
*A61B 5/00* (2006.01)
*A61B 10/00* (2006.01)

(52) U.S. Cl. .................. 705/3; 702/188; 128/923; 600/301

(58) Field of Classification Search .............. 705/2, 705/3; 128/920, 923; 600/300, 301; 379/106.02; 702/181, 188
See application file for complete search history.

(56) References Cited

U.S. PATENT DOCUMENTS

| | | | | |
|---|---|---|---|---|
| 5,911,132 A | * | 6/1999 | Sloane | 705/3 |
| 5,924,074 A | | 7/1999 | Evans | |
| 5,978,466 A | * | 11/1999 | Quattrocchi | 379/265 |
| 6,084,510 A | * | 7/2000 | Lemelson et al. | 340/539.13 |
| 6,085,510 A | * | 7/2000 | McDonnell | 340/539 |
| 6,088,695 A | | 7/2000 | Kara | |
| 6,117,073 A | * | 9/2000 | Jones et al. | 600/300 |
| 6,148,297 A | | 11/2000 | Swor et al. | 707/3 |
| 6,171,237 B1 | | 1/2001 | Avitall et al. | |
| 6,238,337 B1 | * | 5/2001 | Kambhatla et al. | 600/300 |
| 6,277,071 B1 | | 8/2001 | Hennessy et al. | 600/300 |
| 6,385,589 B1 | * | 5/2002 | Trusheim et al. | 705/2 |
| 6,511,424 B1 | * | 1/2003 | Moore-Ede et al. | 600/300 |

FOREIGN PATENT DOCUMENTS

WO WO 02/41761 A2 10/2001

OTHER PUBLICATIONS

Koo; Jun. 28, 2001; Center for Disease Control; NCVHS; www.cdc.gov/od/hissb/010628p2.pdf.*
Kabore et al; Jul. 2001; "Technical Guidelines for Integrated Disease Surveillance".*

(Continued)

*Primary Examiner*—Marc S. Hoff
*Assistant Examiner*—Paul Kim
(74) *Attorney, Agent, or Firm*—McAndrews, Held & Malloy, Ltd

(57) ABSTRACT

A method is disclosed for providing early detection, classification, and reporting of health-related events in a population. The method includes capturing sets of specific emergency room patient information from a subset of the population as the patient information is first electronically entered into, for example, an electronic medical record (EMR). The patient information is pre-processed, transmitted to and stored in a central database in a central computer facility. The patient information is sorted and analyzed by the central computer facility to detect any health-related events in the population and to generate corresponding alerts. The alerts are electronically reported to designated authorities such as health officials and other government authorities such as the CDC.

40 Claims, 4 Drawing Sheets

OTHER PUBLICATIONS

Damon Adams; May 14, 2001; "Database would ease doctors' paperwork on patient safety"; amednews.com; pp. 1-3.*

"Technology's Support of Public Health", Healthcare Informatics (Jan. 2002).

Dana Hawkins, "Early Outbreak Alert", U.S. News & World Report (Nov. 19, 2001).

Sarah A. Klein, "Med Software Gets Bioterrorism Booster", Crain's Online (Feb. 18, 2002).

* cited by examiner

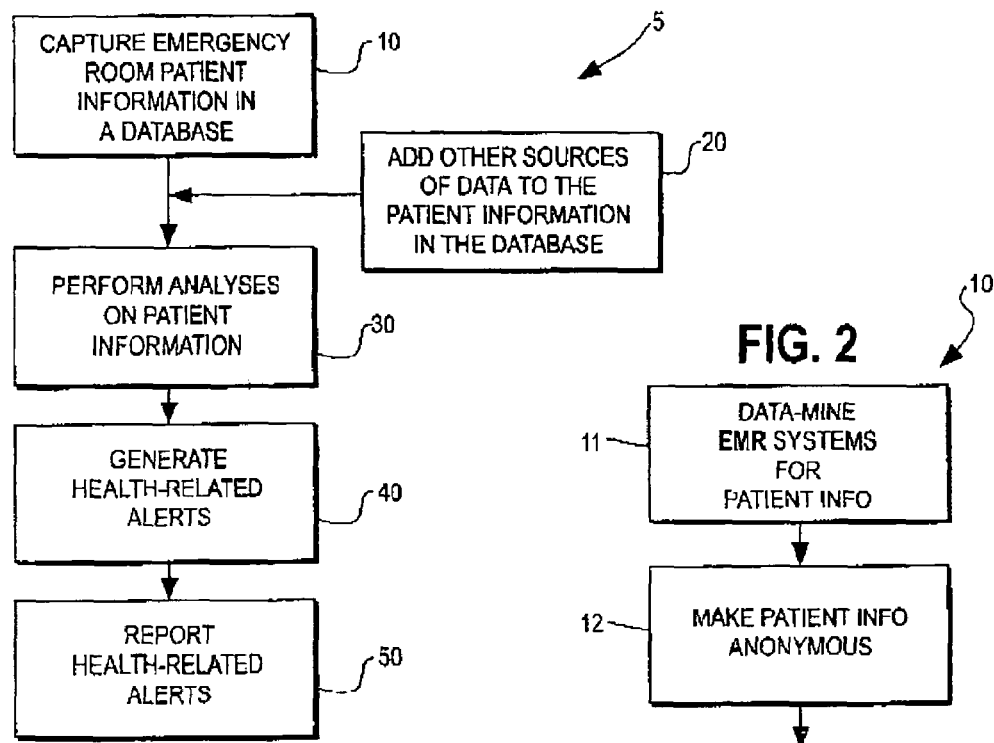
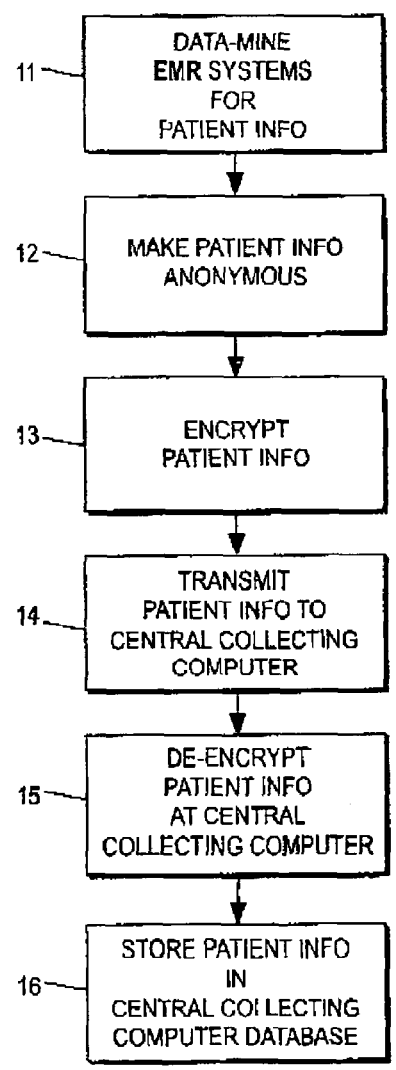

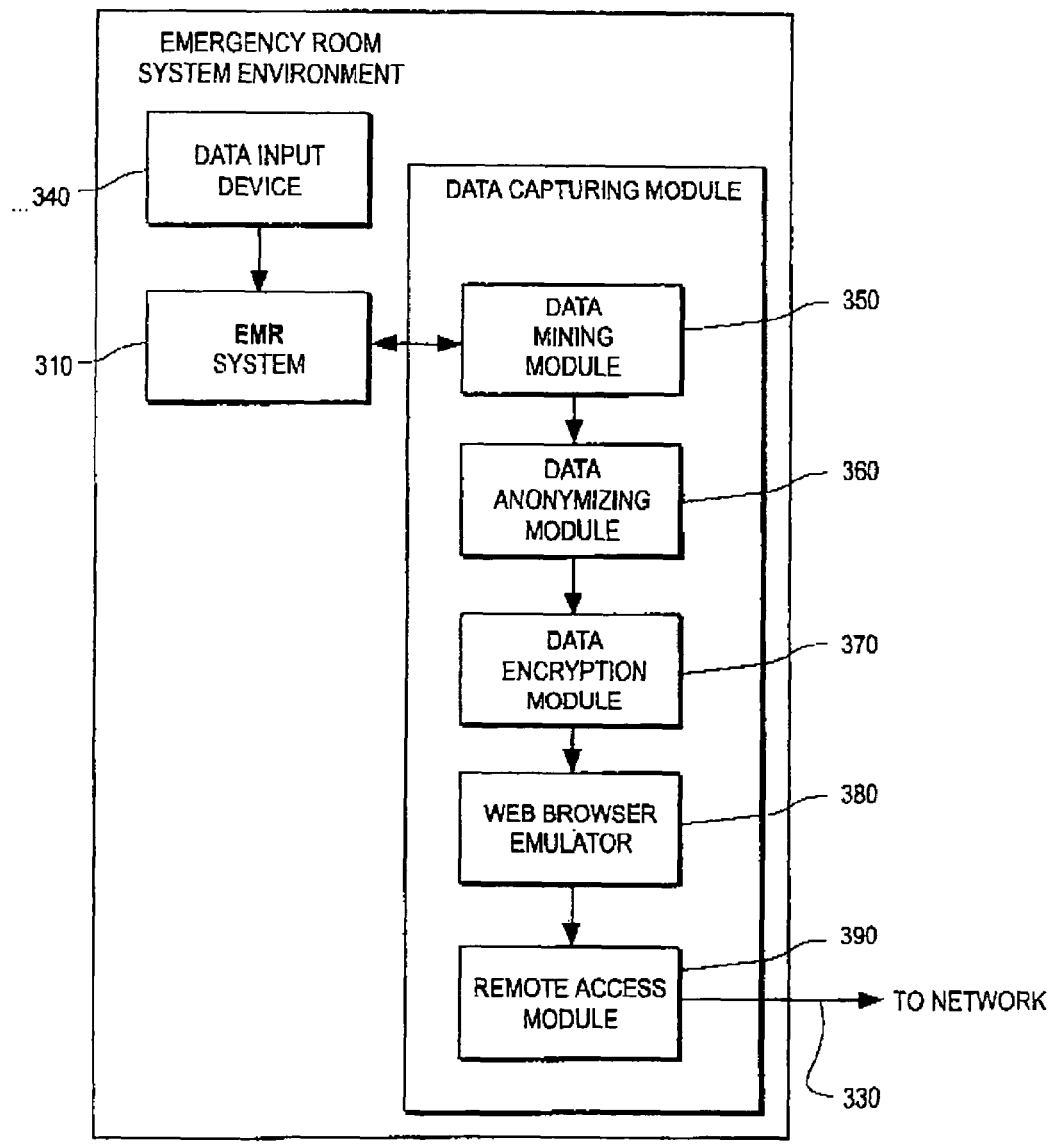

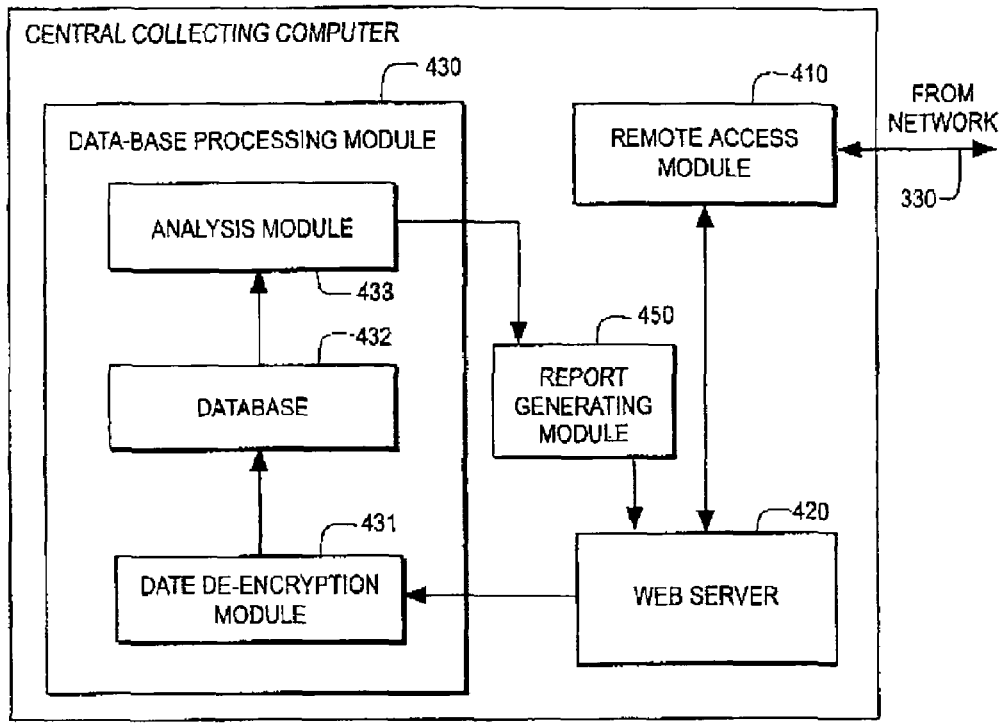
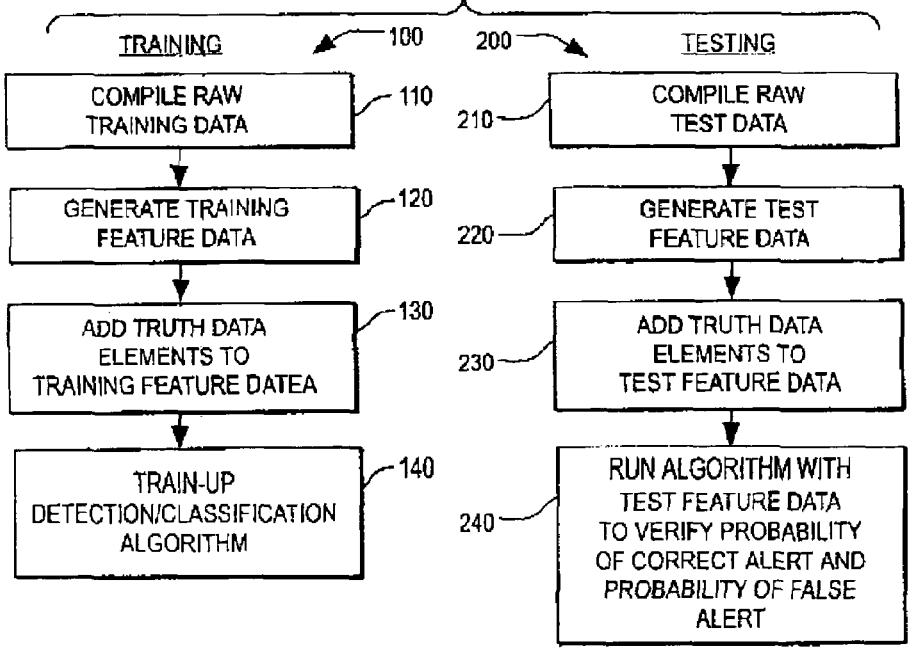

FIG. 6

| PATIENT # | 1 | 2 | 3 | 4 | 5 |
|---|---|---|---|---|---|
| AGE | 13 | 55 | 24 | 62 | 84 |
| SEX | M | F | F | M | F |
| ZIP CODE | 60560 | 61237 | 60478 | 61925 | 61925 |
| COUGH | YES | YES | NO | YES | YES |
| FEVER | NO | YES | NO | YES | YES |
| SHORTNESS OF BREATH | NO | NO | YES | NO | NO |
| WEAKNESS | YES | NO | YES | NO | YES |
| MALAISE | YES | NO | YES | NO | NO |
| BLEEDING | NO | NO | NO | YES | NO |
| RASH | NO | NO | YES | YES | YES |
| PAIN | NO | NO | YES | YES | YES |
| BODY TEMP | 99 | 101 | 98 | 103 | 104 |
| BLOOD PRESSURE | 130/80 | 150/110 | 125/70 | 105/62 | 120/80 |
| HEART RATE | 75 | 50 | 120 | 140 | 135 |

TABLE 1: SETS OF RAW TRAINING DATA (REPRESENTATIVE OF EMERGENCY ROOM PATIENT INFORMATION)

METHODS AND APPARATUS FOR EARLY DETECTION OF HEALTH-RELATED EVENTS IN A POPULATION

BACKGROUND OF THE INVENTION

Certain embodiments of the present invention relate to a method of assessing health-related problems in a community. More particularly, certain embodiments relate to a method of providing early detection, classification, and reporting of new or unusual health-related events in a population based on emergency room patient information.

Monitoring for health-related problems in a community has long been a concern of health officials. Patient information is generated throughout a community in a variety of ways. For example, the information may be in paper form and stored in a file folder, or in electronic form and stored on a computer. However collected and stored, any particular patient's information tends to be isolated from other patient information in the community. Techniques of electronically collecting and accessing information from various locations such as hospitals and other health care centers is well established in the art. The concepts of creating electronic patient files and records and updating those files and records electronically are also well established. Everything from recording patient symptoms and diagnoses to patient scheduling and billing may be accomplished using various medical information systems such as electronic medical record (EMR) systems. Patient information from various sources may be converted to a common format that may be accessed by multiple users at the same time.

For example, ibex Healthdata Systems markets a product called ibex PulseCheck® which is a web-based emergency department information system comprising various modules for doctors, nurses, and administrators. The system interfaces seamlessly with existing systems. Pulsecheck® is able to create a complete Electronic Medical Record (EMR) for a patient from triage to disposition.

Also, U.S. Pat. No. 5,924,074 to Evans is directed to a medical records system that creates and maintains all patient data electronically. The system captures patient complaints, lab orders, medications, diagnoses, and procedures at its source at the time of entry using a graphical user interface. U.S. Pat. No. 6,088,695 to Kara is directed to bar coding medical data so that it may be transported and stored in both physical and electronic form. U.S. Pat. No. 6,171,237 to Avitall et al. is directed to a remote health monitoring system to provide automated administration of health care to a patient at a remote location and is accomplished electronically. U.S. Pat. No. 5,911,132 to Sloane is directed to a method to collect epidemiological transaction records in a central database computer for the purpose of helping to diagnose new patients with similar symptoms to previous patients.

Even though much patient information for a community may exist in electronic form, it is often not gathered and correlated in a discriminating and timely manner to be of any use for determining health-related events affecting the community, especially new or unusual health-related events that require a quick response by health and/or other government officials. For example, the threat of terrorism has recently become a higher concern to government officials. As a result, certain health-related problems arising in a community, such as food poisoning, water contamination, exposure to nuclear radiation, exposure to poison gas, or exposure to unusual biological agents such as anthrax, may not be detected in a timely manner for health officials and other governmental officials to properly react. Emergency room environments are where symptoms of such health-related problems will first be electronically entered.

Real time surveillance of infectious disease outbreaks is essential for the early detection of epidemics. Current surveillance databases require data entry by individual institutions and submission to a central database for processing. There is currently no data management architecture that allows for active extraction of real time data from a multi-institutional network for the detection of disease outbreaks.

Surveillance, as defined by Alexander Langmiur, "means the continued watchfulness over the distribution and trends of incidence through the systematic collection, consolidation, and evaluation of morbidity and mortality reports and other relevant data" for the purpose of detecting, tracking, monitoring, and preventing adverse health-related events.

The Center of Disease Control (CDC) defines public health surveillance as "the ongoing, systematic collection, analysis, and interpretation of health data essential to the planning, implementation, and evaluation of public health practice, closely integrated with the timely dissemination of these data to those who need to know". Collected disease surveillance data are then used by public health professionals, medical professionals, private industry, and interested members of the general public to estimate the magnitude of a health problem, follow trends in its incidence and distribution, detect outbreaks or epidemics, and evaluate control and preventative measures.

There are two general categories of surveillance: passive and active. Passive surveillance is the reporting and confirmation of cases seen in health facilities. In comparison, an active surveillance system is one where case-finding methods are implemented to proactively look for cases. For a successful passive surveillance system, health care providers must be able to correctly identify the clinical manifestations of known diseases with well-defined symptoms and, many times, laboratory confirmation. Passive surveillance has several limitations. In many parts of the rural United States, there is little access to health care facilities, therefore, people who fall ill may not visit a primary care physician and the case goes unreported. There are problems of under-recognition of newly emerging diseases. Laboratory support is often inadequate and/or not standardized. There are often logistical problems in reporting due to unmotivated, untrained, over-worked, and underpaid staff. There is also substantial variation in the quality of surveillance systems from county to county and from state to state.

In 1970, the Surgeon-General of the United States of America declared it, "time to close the book on infectious diseases, declare the war against pestilence won, and shift national resources to such chronic problems as cancer and heart disease". The indifference displayed by public health experts towards threat of communicable diseases in the 1970's led to less financial and manpower support for communicable disease surveillance systems. Consequently, surveillance systems were not initiated or sustained in the United States. New and re-emerging communicable diseases were allowed to flourish unchecked.

With the emergence of new diseases such as HIV/AIDS, West Nile virus, and Hantavirus, and the resurgence of diseases long since considered under control (such as malaria, cholera, and tuberculosis), domestic surveillance systems have had an abrupt reawakening since it is generally agreed that effective public health surveillance is critical for the early detection and prevention of epidemics. There is a clear and urgent need for surveillance of known and existing communicable diseases, especially those with high epidemic potential. Also, there is a clear and urgent need for early recognition of new infections (over 20 new pathogens have been discovered since the mid-1970's). There is also a need to monitor the growing resistance to anti-microbial drugs.

Although improving, the surveillance capacity of the health care system in the United States is poorly developed. In 1989, all state health departments in the United States began communicating notifiable disease data each week to the CDC through the National Electronic Telecommunication Surveillance System (NETSS). Since then, many state agencies have also initiated computer linkages with their local health departments for disease reporting. However, none have real time analysis or reporting.

Although multiple agencies and individuals in the United States have attempted to address the need for current data from emergency care facilities for the purpose of disease tracking, utilization patterns, and disease surveillance, no system exists that conducts real time, active surveillance of a large number of hospitals in the United States. One main obstacle is the lack of unified data collection parameters and the inability to merge and track incoming data from emergency departments of non-related medical institutions. However, by providing a non-intrusive means to obtain patient health data using a "Sentinel Physician" approach to surveillance, the obstacle may be overcome.

A sentinel physician collects and submits medical data on individual patients during the normal course of a doctor's office visit. The usefulness of sentinel physicians for surveillance has been demonstrated in the United Kingdom, Belgium, and other European countries. In France, a computerized physician based network has been implemented for national public health surveillance.

Each of the aforementioned national and international reporting systems has limitations. For example, each surveillance system was disease specific. Each surveillance system was passive in which standardized reporting forms were distributed en mass to physicians and no action was taken unless completed forms were received by the sponsoring public health agency. Hence, low completion rates resulted. Lag time between disease reporting and notification of public health agencies was greater or equal to a week. Physicians needed training in the surveillance process.

Never before has the need for bio-surveillance capacity been so great. The threat of biological attack, combined with the re-emergence of new and variant infectious agents necessitates the development and use of a functional bio-surveillance system. The public health infrastructure at the county, state, and national level must be primed to instantaneously detect and notify authorities of biological or chemical terrorism. An act of terrorism involving the clandestine release of a biological agent is a major public health emergency and would require an immediate response. In comparison to other emergency events, with the current national surveillance system in place, an attack with a biological agent will not be detected at the time the event occurs, nor will it evoke an immediate response from first responders (police, fire, or emergency medical service personnel). This is because an attack with a biological agent is likely to be clandestine; hence, a delay between exposure and onset of symptoms (an incubation period which may be as long as several days, weeks, or months) may be incurred.

The difficulty of early detection is further confounded because diseases caused by many of the likely bio-terrorist agents may not be accurately diagnosed until late in their course, since early symptoms may seem to be non-specific to a treating physician (e.g., a physician with little or no experience with agents such as smallpox or Ebola). Some possible biological agents include smallpox, anthrax: cutaneous, anthrax: pulmonary, viral hemorrhagic fevers (Ebola, Lassa), brucellosis, tularemia, cutaneous plague, pneumonic plague, botulism, Q fever, typhus, and encephalitis. Some possible chemical agents are ricin, sarin, and organophosphates.

A need exists for an approach to capture specific types of emergency room patient information in real time from throughout a community and process the information to detect, classify, and report health-related alerts for a population in the community in a timely manner. A need also exists to develop a robust algorithm for detecting and classifying a plurality of health-related events in the community with a low probability of false alert and a high probability of correct alert.

BRIEF SUMMARY OF THE INVENTION

An embodiment of the present invention provides a method for providing early detection and reporting of health-related events in a population. The method includes capturing sets of specific emergency room patient information, in real time, from a subset of the population as the patient information is first electronically entered for electronic recording in an emergency room environment to generate patient database information. The patient information includes initial patient complaints and symptoms instead of diagnoses. The patient information is analyzed to generate health-related alerts. The alerts are electronically reported to designated authorities such as health officials and other government authorities such as the CDC.

Also, a method is provided for generating an algorithm providing early detection and classification of health-related events in a population. The method includes compiling sets of raw training data representative of specific types of patient information gathered electronically during emergency room visits. Sets of training feature data are generated based on the sets of raw training data. A training truth data element is added, corresponding to a correct diagnosis of disease or injury, to each set of training feature data. A detection/classification algorithm is then trained-up in response to the sets of training feature data.

Apparatus is also provided for early detection and reporting of health-related events in a population. The apparatus includes an emergency medical record (EMR) system for electronically recording patient information in an emergency room environment, a data capturing module connected to the EMR system to capture the patient information from the EMR system and format the patient information as a web request, a network connected to the data capturing module to transport the web request as packets of data over the network, and a central collecting computer connected to the network to receive and store the packets of data.

Certain embodiments of the present invention afford an approach to capture emergency room patient information from throughout a community in real time and process the information to detect, classify, and report health-related alerts for a population in the community. Certain embodiments also afford an approach to develop a robust algorithm for detecting and classifying such health-related events in the community with a low probability of false alert and a high probability of correct alert.

BRIEF DESCRIPTION OF THE DRAWINGS

FIG. 1 is a flowchart illustrating a method to provide early detection, classification, and reporting of health-related events in a population in accordance with an embodiment of the present invention.

FIG. 2 is a flowchart illustrating the data capturing part of the method of FIG. 1 in accordance with an embodiment of the present invention.

FIG. 3 is a schematic block diagram illustrating apparatus for implementing certain steps of the method of FIG. 1 and FIG. 2 in accordance with an embodiment of the present invention.

FIG. 4 is a schematic block diagram illustrating apparatus for implementing certain other steps of the method of FIG. 1 and FIG. 2 in accordance with an embodiment of the present invention.

FIG. 5 is a flowchart illustrating a method to develop an algorithm to detect and classify health-related events occurring in a population of a community in accordance with an embodiment of the present invention.

FIG. 6 is an exemplary set of possible raw training data.

The foregoing summary, as well as the following detailed description of certain embodiments of the present invention, will be better understood when read in conjunction with the appended drawings. It should be understood, however, that the present invention is not limited to the arrangements and instrumentality shown in the attached drawings.

DETAILED DESCRIPTION OF THE INVENTION

FIG. 1 is a flowchart illustrating a method 5 to provide early detection, classification, and reporting of health-related events in a population in accordance with an embodiment of the present invention. In step 10, emergency room patient information is captured from various emergency rooms in a community and stored in a central database at a central data collecting facility. In step 20, other sources of data are merged into the database that may be related to the emergency room patient information. For example, once a patient's zip code is verified within the database, socio-economic data and neighborhood demographic data may be merged into the patient's database record. In step 30, the patient information in the database is processed and analyzed using various techniques to determine if anything unusual is going on in the community. In step 40, health-related alerts are generated if the analyses in step 30 finds anything unusual. In step 50, any health-related alerts are reported in a standardized report format to designated authorities such as the CDC and the military.

The emergency room patient information may include but is not limited to patient contact information (phone, address, etc.); triage information; initial patient interview information including basic patient demographic information such as patient age, sex, and zip code and patient presenting symptoms including chief complaint, vital signs, and results from point of care testing (hemoglobin, urinalysis) and smart bio-detector chip technology.

The smart bio-detector chip technology is used to discern a bio-agent from a multitude of natural human infections. A bio-detector chip is a proposed diagnostic technology that is capable of identifying pre-symptomatic infected persons. The dilemma in the detection of bio-agents in large patient volume emergency departments is the fact that the bio-agent is an unusual, unidentified agent among many common agents. For example, in February 2000, emergency rooms were filling up with influenza patients. It was assumed that a patient with flu-like symptoms had been infected with influenza. But, hypothetically, the symptoms could have been due to any one of the eight top bio-agents with similar symptoms that was used in a covert terrorist attack.

Since the bio-detector chip technology is non-intrusive (working with a sample collected from a patient during a routine clinical screening), comprehensive (capable of identifying up to a million distinct genetic signatures imbedded on a two centimeter by two centimeter chip), and disposable, routine screening using the technology may be considered standard care in participating hospitals. Therefore, in order to detect the occasional biohazard agent amongst the thundering herd of normal cases of influenza, for example, the miniaturized bio-detector chip may be used to provide immediate diagnosis of diseases documented in a Bio-Print database (a comprehensive genomic and proteomic profile of both conventional agents as well as bio-agents), flagging man-made and/or unusual diseases to the central collecting facility before there are any confirmatory symptoms. In the "front line", smart bio-detector chip technology detects any undesirable bio-agents.

A smart bio-detector chip may include a matrix of many cells that are each associated with, for example, a different anti-body. When the chip is exposed to a biological sample, a bio-agent present in the sample attaches itself to a cell of the chip having the anti-body corresponding to that bio-agent. In one version of the technology, the attachment of the bio-agent to an anti-body of a particular cell of the chip causes an optical index of refraction to change for that cell. When impinging light is reflected off of the cell, it will reflect at a different angle with the bio-agent attached than when the bio-agent is not attached. The difference in the reflected angle is detected and converted to an electrical output for that cell, indicating that the particular bio-agent is present in the sample. The process is known as surface plasma resonance.

The other sources of data collected and merged into the database may include but are not limited to patient medical history, patient current and past medications, patient lab results (blood tests, urine tests, etc.), results of any medical procedures (e.g. X-rays, MRI, etc.), discharge diagnoses, and supplementary data. The supplementary data may include number and type of 911 dispatches, emergency department diversions, number and type of calls to nurse/medical call centers, number and type of calls to poison control centers, number and types of over-the-counter pharmacy sales, number and type of non-emergency hospital admissions/diagnoses, results of medical examiners reports, number and duration of absenteeism in public/private schools, morbidity and mortality of domestic and wild animals, and climatic data from weather stations.

FIG. 2 is a flowchart illustrating the data-capturing step 10 of the method 5 of FIG. 1 in accordance with an embodiment of the present invention. In step 11, data mining is performed to collect the emergency room patient data from, for example, existing electronic medical record (EMR) systems in various emergency rooms throughout a community. Data mining involves accessing the data recorded in the EMR systems through an electronic interface and extracting that data corresponding to the patient information of interest as described above. Data mining is performed continuously such that patient information is accessed from the EMR systems in the various emergency rooms almost immediately after the patient information is first entered.

In step 12, the patient information that has been data mined is stripped of certain identifying information, such as the patients' names, to make the information anonymous. As a result, patient confidentiality is maintained. In step 13, the patient information is then encrypted (encoded) to make the information even more secure for subsequent data transmission. In an embodiment of the present invention, the patient information is encrypted using triple DES, the digital encryption standard used by many organizations including the United States government. The level and type of encryption may be flexible, however, as to accommodate new standards and/or encryption technologies that may come along in the future.

In step 14, the patient information is transmitted over a network, such as the Internet, to a central collecting computer containing the central database. Upon reception of the patient information by the central collecting computer, the patient information is de-encrypted (decoded) in step 15. The patient information is then integrated into the database, in step 16, on the central collecting computer where the information is stored.

When patient information is extracted from an EMR system through data mining, the data mined information may be checked for completeness (i.e., all the required information has been found). For example, the patient information may not be sent to the central collecting computer if the basic patient demographic information has not been found in the EMR system for a given patient. Also, upon reception of the patient information by the central collecting computer, the data may again be checked for completeness to make sure no information was lost during transmission.

FIG. 3 and FIG. 4 are schematic block diagrams illustrating apparatus for implementing the steps of the methods of FIG. 1 and FIG. 2 in real time in accordance with an embodiment of the present invention. Referring to FIG. 3, an emergency room system environment 300 comprises an EMR system 310, a data capturing module 320, and a data input device 340. The data input device 340 is connected to the EMR system 310. Patient information is entered into the EMR system 310 through the data input device 340 in an emergency room environment. The EMR system 310 may interface to the data capturing module 320 through any of a variety of well-known computer-to-computer interfaces. In one embodiment of the present invention, the data capturing module and EMR system are both integrated into the same computer hardware platform as software modules.

The data capturing module 320 includes a data mining module 350, a data anonymizing module 360, a data encryption module 370, a web browser emulator 380, and a remote access module 390. The data mining module 350 extracts patient information from the EMR system 310 in real time as it is entered into the EMR system. The data mining module 350 then passes the information to the data anonymizing module 360 where the patient data is stripped of certain identifying patient information such as patient name. The patient information is then encrypted by the data encryption module 370. The Web browser emulator 380 receives the encrypted patient information and formats the patient information into a web request to be transmitted over a network. In one embodiment of the present invention, the web request comprises a single get transaction with the appropriate header information. The remote access module 390 accepts the web request and transmits it out over a network 330. The network 330 may be the Internet, intranet, or some other type of communication network. In certain embodiments of the present invention, the remote access module 390 may also receive data from the network 330 such as health-related alerts and reports and store them on a server in the emergency room system environment 300.

The network 330 comprises the physical interface and software between the emergency room system environment 300 and a central collecting computer 400 (see FIG. 4). The network may include telephone lines, routers and switchers, fiber optic cable, radio transmitters and receivers, or any other devices and software that may be used to establish a communications link between the emergency room system environment 300 and a central collecting computer 400. Typically, the network 330 comprises the Internet and the World Wide Web (WWW). The web browser emulator 380 is a program that serves as a front-end to the WWW on the Internet.

A system physically connects to a network through a port. The data capturing module 320 may connect to a network 330 through, for example, a serial port. A modem is a device that converts information between the digital signals of a computer and the analog signals of telephone lines and vice-versa. Information from the web browser emulator 380 passes through the serial port on the digital side of the modem (i.e. between the browser and the modem). Communication with the modem is established by employing software that is known as a point-to-point (PPP) protocol. The PPP protocol is a standard protocol that allows multiple network protocols to be used over a serial connection such as a modem line. A network port and related functionality are provided by the remote access module 390.

Information is formatted and transferred across a network using software controlled communications protocols such as TCP/IP (Transmission Control Protocol/Internet Protocol). The IP protocol controls the routing of information through the network and the TCP protocol controls the actual transfer of information (packets) over the network.

The central collecting computer 400 includes a remote access module 410 to receive data from the network 330 and to transmit data through the network. The remote access module 410 connects to a web server 420. The web server 420 accepts the requests from the various emergency room environments connected to the network 330 and interprets the requests and extracts the patient information. Other related patient information from other institutions may also come in to the central collecting computer 400 to be integrated into the database. The web server connects to a database processing module 430. The database processing module includes a data de-encryption module 431, a database 432, and an analysis module 433.

In general, a web server provides World Wide Web (WWW) services on the Internet. A web server includes the hardware, operating system, web server software, TCP/IP protocols and web site content. The web server software manages web page requests from the browsers and delivers HTML documents (reports) in response. The web server may also execute server-side scripts that provide functions such as data base searching.

The extracted patient information comes into the data de-encryption module 431 from the web server 420 and is decoded. The decoded patient information may be checked for completeness and is then integrated into the database 432 in the form of database records. The analysis module 433 extracts patient information from the database 432 and processes the patient information in order to generate health-related alerts and other related data if the analysis module detects anything unusual going on in the population.

Results of the analysis may be transferred to a report generating module 450. The report generating module 450 formats alerts and related information into a logical, readable, standardized format. The web server 420 also is able to transmit reports out over the network 330 to the various emergency room environments and designated authorities. Again, the reports are generated by report generating module 450 based on information stored in the database processing module 430 and analysis performed by the analysis module 433.

Various types of analyses may be provided by the analysis module 433 to generate health-related alerts and other related data. For example, traditional epidemiological analysis may be performed on the incoming patient data. Traditional epidemiological analysis may include calculating a total number of cases; determining incident rates of cases; determining prevalence rates; determining time trends; and levels of risk to a population. Traditional epidemiological analysis may also include performing regression analysis on the patient information. Results of the regression analysis may include magnitude and distribution of an epidemiological outbreak; time, location, and mode of exposure; demographics of affected persons; vehicle of exposure; and persons at risk for disease.

Another example of analysis that may be performed by the analysis module 433 is mapping analysis. Mapping analysis may include generating spot dot maps showing the actual location of epidemiological cases; generating density maps showing number of epidemiological cases per spatial area; generating rate maps showing spatial areas having low, medium, and high rates of mortality; and generating cluster maps showing time segments and spatial areas having unusually high numbers of epidemiological cases within close temporal and spatial proximity to each other.

Still a further example of analysis that may be performed by the analysis module 433 is clinical syndrome analyses. Clinical syndrome analysis analyzes clinical syndromes/symptoms rather than specific diagnoses and/or laboratory-confirmed cases for the early detection of adverse health events. Clinical syndrome analysis may include applying statistical techniques to the patient information in the database 432 to generate health-related alerts. Certain statistical parameters such as means and standard deviations may be calculated from the patient data and compared to predetermined thresholds to determine if anything unusual is going on within a population. Clinical syndrome analysis may also include generating feature data from the patient information stored in the database and running a detection/classification algorithm on the feature data to generate health-related alerts if anything unusual is going on in a population. The detection/classification algorithm may be previously generated by training-up the algorithm. Training up the algorithm may include any of manually developing a set of mathematical functions, applying back-propagation neural network techniques, and applying evolutionary processing techniques.

FIG. 5 is a flowchart illustrating a method 100 to generate an algorithm to detect and classify health-related events occurring in a population of a community in accordance with an embodiment of the present invention. Such an algorithm may be used in the analysis step 30 of FIG. 1 by the analysis module 433 of FIG. 4. The steps of the method 100 comprise the step 110, compiling sets of raw training data, the step 120, generating sets of training feature data, the step 130, adding truth data elements to the sets of training feature data, and the step 140, training-up a detection/classification algorithm.

In the step 110, sets of raw training data are compiled. Each set of raw training data corresponds to a patient, real or fabricated, that has entered an emergency room with symptoms. The raw training data comprises patient demographic and clinical information. The demographic information may include the age of the patient, the sex of the patient, and the zip code of where the patient resides. The clinical information may include chief complaints of the patient as well as vital signs of the patient. For example, the chief complaints may include coughing, a fever, shortness of breath, weakness, malaise, bleeding, a rash, and pain. The vital signs may include, for example, body temperature, tachycardia (rapid heart beat), hypotension (decreased or lowered blood pressure), hypertension (elevated blood pressure), and reduced heart rate. Table 1 in FIG. 6 illustrates an example of five possible sets of raw training data corresponding to five emergency room patients.

The raw training data may be compiled from real patient data taken from emergency room locations and/or other sources. The raw training data may also be fabricated based on expected or likely scenarios. Studies and analysis may be performed by, for example, research institutions to develop the expected or likely scenarios for certain illnesses and injuries. Data based on likely scenarios may have to be used for illnesses and injuries due to rare events such as exposure to nuclear radiation or bio-terrorism agents. In practice, a large number of sets of raw training data may be required to generate a robust algorithm. The number of sets may be in the hundreds or even thousands.

Once sets of raw training data are compiled for one or more health-related events, in the step 120 the sets of raw training data may be converted to sets of training feature data. For example, the training feature data may include averages of certain demographic and clinical raw training data. Other statistical parameters, such as standard deviations, may be generated as training feature data. Simple differences or complex functions may be used to generate the training feature data. Much of the raw training data itself may be included in the sets of training feature data.

In general, generation of the training feature data from the raw training data is based on direct a priori knowledge, logical deductions, and/or detailed analytical studies. The key is to try to generate training feature data that allows the resultant detection/classification algorithm to generate health-related alerts with a high probability of a correct alert and a low probability of a false alert. For example, an acceptable probability of correct alert for an anthrax outbreak may be greater than 90% and an acceptable probability of false alert may be less than 1%. The acceptable probabilities may be different for different types of alerts.

In the step 130, truth data elements (i.e. diagnostic information) are added to the training feature data such that the true condition of each patient is identified. For example, in Table 1 of FIG. 6, patient #1 may have influenza, patient #2 may have a common bacterial infection, patient #3 may have a common virus, and patients #4 and #5 may have nerve gas poisoning. The truth diagnoses are entered into a data table along with the training feature data. By having the true diagnosis of the patient associated with the patient's set of training feature data, the complete set of training feature data, which includes the truth data, is used to train-up an algorithm that may accurately detect and classify the occurrence of a health-related event in a population.

In the step 140 of the method 100, the algorithm is trained-up using the previously generated sets of training feature data. As described herein, the term training-up may include:

1. generating the algorithm by manually developing a set of mathematical functions, relationships, and rules based on studying the sets of training feature data.

2. generating the algorithm by applying back propagation neural network techniques using the training feature data.
3. generating the algorithm by applying evolutionary processing techniques using the training feature data.

Manually developing a set of mathematical functions and relationships may entail recognizing simple statistical relationships between different health-related events and the training feature data. Simple functions of statistical parameters may be developed using, for example, means and standard deviations and comparing results of the functions to pre-determined thresholds. If the output of a function is greater than the threshold, the alert state is asserted (detection and/or classification of a particular health-related event). If the output of the function is less than or equal to the threshold, the alert state is not asserted (no detection of a particular health-related event). The manual approach is more appropriate for those health-related events whose training feature data tend to be more easily discriminated from the training feature data of other health-related events.

In cases where the training feature data between different health-related events is more subtle, more sophisticated techniques may be employed to generate an algorithm that may discriminate between the different health-related events. For example, the raw training data (i.e. clinical symptoms and demographic information) for two health-related events such as food poisoning and exposure to nuclear radiation may be very similar. It may be very possible to discriminate between the two events but the mode of discrimination may not be readily obvious in the raw training data or resultant training feature data.

Techniques using back propagation neural networks and/or evolutionary processing such as genetic algorithms may be applied to the training feature data to generate a function/algorithm that is able to reliably discriminate between the seemingly similar data of the multiple events. There are many neural network and genetic algorithm tools to choose from on the market that may be used to train up a detection/classification algorithm. One neural network product that may be used is called NeuroSolutions developed by NeuroDimension, Inc. Similarly, genetic algorithm products called Genetic Server and Genetic Library, also by NeuroDimension, Inc., may be used.

The error back-propagation neural network technique is a very popular technique to generate an algorithm (i.e. a neural network algorithm) that yields desired outputs when presented with particular inputs. Feed forward neural networks trained by back-propagation include several layers of simple processing elements called neurons, interconnections, and weights that are assigned to the interconnections. Each neuron comprises the weighted sum of its inputs filtered by a transfer function. The neurons are connected to each other such that information relevant to the input/output mapping is stored in the weights. The different layers of neurons in back-propagation networks receive, process, and transmit information concerned with the relationships between the input parameters (training feature data) and corresponding output results (alerts). Neural networks also comprise one or more hidden layers of neurons that do not directly interact with the input data or output data. Instead, the hidden layers aid in performing non-linear detection and classification on information provided by the input and output layers.

In the back-propagation technique, the network begins with a random set of weights. Output values are generated based on the weights and connections of the neurons as the input data (training feature data) is fed forward through the neural network. The output values are compared with the truth data (what the outputs truly should be if the neural network is correctly generating the alerts). The difference between the generated output values and the true output values determines the overall error of the neural network algorithm. The network attempts to minimize the error by adjusting the weights of the errors in the direction of decreasing error. Theoretically, after many iterations of the process, the error is reduced to an acceptable level corresponding to an acceptable probability of a false alert.

Back-propagation neural network techniques are well known and may be easily applied to generate a detection/classification algorithm to discern between various health-related alerts. The key is to start with good sets of raw training data and subsequent good sets of training feature data. If the training feature data contains enough variation between different health-related events (i.e. have good sets of training data), a neural network algorithm may be trained-up that is able to reliability discriminate between the events, such as cases of food poisoning and cases of exposure to nuclear radiation in a population.

The genetic algorithm technique is a newer technique to generate an algorithm that yields desired outputs when presented with particular inputs. Genetic algorithm techniques are inspired by Darwin's theories on evolution. Desired outputs, for a given set of inputs, are effectively evolved over many iterations or generations. The technique initially generates a random population of solutions for the problem, which may or may not (likely not) be suitable solutions. The fitness of each solution in the population is determined (i.e. an error is generated as the difference between the actual outputs and the true, desired outputs, similar to what is done for neural networks). A new or updated population of solutions is generated by performing genetic or evolutionary operations on the sets of solutions in the original population. Some of the typical genetic operations used include:

1. selection—select two parent solutions from a population according to their fitness (the better the fitness, the greater the chance to be selected).
2. crossover—with a pre-defined probability of crossover, cross over the parents to form a new offspring solution (children solutions). If no crossover is performed, the offspring are exact copies of the parents.
3. mutation—with a pre-defined probability of mutation, mutate new offspring at each position in the solution.
4. accepting—place new offspring solutions in a new population of solutions.

The resultant new population of solutions is tested and the fitness (errors) is again determined. The process iterates in a similar manner until the error for a particular solution in the latest generation of solutions is acceptably low, corresponding to an acceptable probability of a false alert. As a result, a solution to the detection/classification problem may be trained-up. Again, the key is to start with good sets of raw training data and subsequent good sets of training feature data. If the training feature data contains enough variation between different health-related events, though they may be subtle or undetectable differences to a person manually studying the data, genetic algorithm techniques may be used to train-up an algorithm that is able to reliably discriminate between the different events.

The method 200 of FIG. 5 illustrates how to test the trained up algorithm on an independent set of test data. In the step 210, an independent set of raw test data is compiled. The raw test data may be compiled from real patient data taken from emergency room locations and/or other sources.

The raw training data may also be fabricated based on expected or likely scenarios. Care must be taken, however, to introduce realistic differences (unique sets) in the raw test data such that it is not simply a duplication of the raw training data. As a result, the robustness of the algorithm may be characterized.

In the step 220 of the method 200, test feature data is generated from the raw test data using the same feature definitions as for the training data. In the step 230, truth data elements are added to the test feature data as was done for the training feature data. In the step 240, the algorithm is run on the sets of test feature data including the truth data elements. The performance of the algorithm is evaluated by calculating a probability of false alert and a probability of correct alert. Other sets of raw test data may be compiled and tested on the algorithm and an average performance of the algorithm may be determined over the multiple sets of test data.

The algorithm training techniques described above allow for a robust detection and classification algorithm to be generated that may clearly discriminate between various possible health-related events. Known signatures of health-related events are not searched for in a database. Instead, incoming data is translated into input parameter data that is then presented to the input of a detection/classification algorithm. The algorithm outputs alerts with pre-determined probabilities of false alarm and correct alarm.

The algorithm is able to discriminate between subtle differences in the incoming data and generate correctly classified alerts. The incoming data does not have to correspond to some exact known signature of a health-related event. A health-related event may manifest itself in a community with a variety of slightly differing signatures that may be very close to the signatures of a totally different health-related event. An algorithm generated using the neural network or genetic algorithm techniques with robust sets of training data may prove to be especially good at discriminating between subtle differences of health-related events.

A resultant algorithm may actually be quite complex and actually comprise several smaller algorithms or functions. For example, part of a resultant algorithm may perform detection functions. The detection functions may simply indicate that something new is going on in a community that was previously not present. The detection functions may then trigger classification functions that attempt to discriminate between various possible health-related events.

Detection and classification functions of an algorithm may be broken down even further. For example, a first function of the algorithm may discriminate between bio-related and non-bio-related events. A second function may then discriminate between bacterial-related and viral-related events. Once that decision is made, a third function may discriminate between the different types of possible bacterial-related events and generate an alert for bacterial meningitis.

The various steps of the methods described herein may be implemented on dedicated hardware modules such as circuit boards with digital signal processors or may be implemented as software modules running on a general purpose computer or processor such as a commercial, off-the-shelf PC or workstation. The implementations of the various steps of the methods described herein may be combined or separated in modules according to various embodiments of the present invention. For example, the emergency room system environment 300 of FIG. 3 may be implemented on a commercial PC running software or may include several computers or discrete pieces of hardware such as digital signal processors implementing the various functions.

Confirmation of generated alerts and follow up with laboratory testing of infectious agents to confirm suspicion of infectious agents may also be performed by the central processing computer 400. Demographic and epidemiological profiles of an outbreak may also be confirmed to distinguish possible bio-threats from naturally occurring outbreaks.

In summary, the advantages and features include, among others, the ability to detect, classify, and report health-related alerts for a population in the community in real time. Certain embodiments also afford an approach to develop a robust algorithm for detecting and classifying such health-related events in the community with a low probability of false alert and a high probability of correct alert.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for providing early detection and reporting of health-related events in a population, said method comprising:

automatically capturing patient information from a plurality of members of said population, as said patient information is first electronically entered for electronic recording in a plurality of emergency room environments, to generate patient database information at a central collecting location, wherein said capturing comprises data-mining for said patient information in a plurality of emergency medical record (EMR) systems at a plurality of respective emergency room sites by continuously accessing patient information recorded in said EMR systems through an electronic interface and extracting data corresponding to said patient information;

performing analyses on said patient database information of said plurality of members to generate a health-related alert; and reporting said health-related alert to designated authorities.

2. The method of claim 1 wherein said patient information includes:

emergency room patient triage information;
patient contact information; and
initial patient interview information.

3. The method of claim 2 wherein said emergency room patient triage information comprises:

instances of basic patient demographic information; and
instances of basic patient clinical information.

4. The method of claim 3 wherein said instances of basic patient demographic information comprises:

patient age;
patient sex; and
patient zip code.

5. The method of claim 3 wherein said instances of basic patient clinical information comprise at least one of:

chief complaint including any of cough, fever, shortness of breath, weakness, malaise, bleeding, rash, and pain;

vital signs including any of body temperature, tachycardia, hypotension, blood pressure, and heart rate; and smart bio-detection chip results.

6. The method of claim 1 wherein said capturing is accomplished electronically over a network from a plurality of emergency rooms.

7. The method of claim 1 wherein said capturing comprises:
sending said patient information, from each of said plurality of emergency room sites, over the Internet as at least one packet of information;
receiving said at least one packet of information, for each of said plurality of emergency room sites, in a web server on a central collecting computer; and
storing said patient information on said central collecting computer as said patient database information.

8. The method of claim 7 further comprising:
verifying said patient information for completeness before said sending;
stripping said patient information of certain personal patient data, including patient name, before said sending to make said patient information anonymous;
encrypting said patient information before said sending, to make said patient information secure;
de-encrypting said patient information after said receiving; and
verifying said patient information after said de-encrypting.

9. The method of claim 7 further comprising integrating related patient data, from other data sources external to said central collecting computer, with said patient database information on said central collecting computer.

10. The method of claim 9 wherein said related patient data comprises:
patient historical medical data;
patient historical and current medications;
patient laboratory results; and
patient diagnostic results.

11. The method of claim 1 wherein said performing analyses includes performing clinical syndrome analyses on said patient database information including clinical symptoms information.

12. The method of claim 11 wherein said performing clinical syndrome analyses includes generating a set of patient feature data from said patient database information.

13. The method of claim 12 wherein said performing clinical syndrome analyses includes running a detection/classification algorithm on said patient feature data to generate said alerts.

14. The method of claim 13 wherein said detection/classification algorithm is trained-up on sets of training feature data representative of said patient information.

15. The method of claim 11 wherein said performing clinical syndrome analyses includes applying statistical techniques to said patient database information to generate said alerts.

16. The method of claim 1 wherein said performing analyses includes performing traditional epidemiological analyses.

17. The method of claim 16 wherein said performing traditional epidemiological analyses includes at least one of:
calculating a total number of epidemiological cases;
determining incident rates of epidemiological cases;
determining prevalence rates of epidemiological cases;
determining time trends of epidemiological cases; and
determining levels of risk to a population.

18. The method of claim 16 wherein said performing traditional epidemiological analyses includes performing regression analysis.

19. The method of claim 18 wherein results of said performing regression analysis include at least one of:
magnitude and distribution of an epidemiological outbreak;
time, location, and mode of exposure;
demographics of affected persons;
vehicle of exposure; and
persons at risk for disease.

20. The method of claim 1 wherein said performing analyses includes performing mapping analysis.

21. The method of claim 20 wherein said performing mapping analysis includes at least one of:
generating spot dot maps showing actual location of epidemiological cases;
generating density maps showing number of epidemiological cases per spatial area;
generating rate maps showing spatial areas having low, medium, and high rates of mortality;
generating cluster maps showing spatial areas having unusually high numbers of epidemiological cases within close spatial proximity to each other;
generating cluster maps showing time segments having unusually high numbers of epidemiological cases within close temporal proximity to each other; and
generating cluster maps showing time segments and spatial areas having unusually high numbers of epidemiological cases within close temporal and spatial proximity to each other.

22. The method of claim 1 further comprising generating reports based on said proximity analyses.

23. The method of claim 1 wherein said reporting is accomplished electronically over a network from a central collecting facility to said designated authorities.

24. The method of claim 1 wherein said generating health-related alerts includes generating an alert for at least one bio-terrorism event if said performing analyses indicates that said bio-terrorism event has occurred in said population.

25. The method of claim 24 wherein said at least one bio-terrorism event is due to at least one of anthrax, small pox, viral hemorrhagic fever, brucellosis, tularemia, plague, botulism, Q fever, typhus, and encephalitis.

26. The method of claim 1 wherein said generating health-related alerts includes generating an alert for an event wherein said event includes at least one of food poisoning, water contamination, exposure to nuclear radiation, and exposure to chemical agents if said performing analyses indicates that said event has occurred in said population.

27. The method of claim 1, wherein capturing patient information comprises automatically collecting said patient information from a plurality of emergency medical record systems, wherein automatically collecting said patient information comprises collecting said patient information without human intervention at said plurality of emergency medical record systems.

28. The method of claim 1, wherein capturing patient information comprises automatically communicating said patient information from a plurality of emergency medical record systems to a central collecting computer, wherein automatically communicating said patient information comprises communicating said patient information without human intervention at said plurality of emergency medical record systems.

29. The method of claim 28, wherein automatically communicating said patient information comprises communicating said patient information to the central collecting computer as a web request.

30. The method of claim 1, wherein capturing patient information comprises executing a data capturing module coupled to an emergency medical record system of the emergency room environment, wherein the data capturing module automatically, without human intervention at said emergency medical record system, obtains said patient information from the emergency medical record system and communicates said patient information to a central collecting computer.

31. The method of claim 30, wherein said data capturing module comprises a software module executing on said emergency medical record system.

32. The method of claim 30, wherein the data capturing module extracts patient information from the emergency medical record system in real-time as patient information is entered into the emergency medical record system.

33. Apparatus for providing early detection and reporting of health-related events in a population, said apparatus comprising:
- a plurality of emergency medical record (EMR) systems for electronically recording patient information in respective emergency room environments;
- a plurality of respective data capturing modules connected to said plurality of EMR systems to capture said patient information from said plurality of EMR systems and format said patient information as a web requests, wherein each of said plurality of respective data capturing modules is adapted to data-mine for said patient information by continuously accessing patient information recorded in a respective connected EMR system through an electronic interface and extracting data corresponding to said patient information;
- a network connected to said data capturing modules to transmit said web requests as at least one packet of data over said network; and
- a central collecting computer connected to said network to receive and store said at least one packet of data.

34. The apparatus of claim 33, wherein each of said plurality of EMR systems further comprises a data input device to electronically enter said patient information into said EMR system.

35. The apparatus of claim 33 wherein each of said plurality of respective data capturing modules comprises:
- a data mining module connecting to said respective connected EMR system to search for and extract said patient information from said respective connected EMR system;
- a data anonymizing module connecting to said data mining module to strip said patient information of certain identifying patient data including patient name;
- a data encryption module connecting to said data anonymizing module to encode said patient information for security;
- a web browser emulator connected to said data encryption module to format said patient information into said web request for transmission over said network; and
- a remote access module connected between said web browser emulator and said network to transmit said at least one packet of data over said network.

36. The apparatus of claim 33 wherein said network comprises at least one of the Internet and an intranet.

37. The apparatus of claim 33 wherein said central collecting computer comprises:
- a remote access module connecting said central collecting computer to said network to receive said at least one packet of data as said web requests from said network;
- a web server connecting to said remote access module to interpret said web request and to extract said patient information from said web requests; and
- a database processing module connecting to said web server to store said patient information extracted from said web requests.

38. The apparatus of claim 37 wherein said database processing module comprises:
- a data de-encryption module to decode said patient information;
- a database to store said patient information; and
- an analysis module to analyze said patient information and generate said health-related alerts.

39. The apparatus of claim 38 wherein said central collecting computer further comprises a report generating module to generate health-related reports in response to said patient information and analysis performed by said analysis module.

40. The apparatus of claim 39 wherein said central collecting computer sends said health-related reports over said network to designated authorities.

* * * * *

UNITED STATES PATENT AND TRADEMARK OFFICE
CERTIFICATE OF CORRECTION

| | | |
|---|---|---|
| PATENT NO. | : 7,024,370 B2 | Page 1 of 1 |
| APPLICATION NO. | : 10/106841 | |
| DATED | : April 4, 2006 | |
| INVENTOR(S) | : John Epler et al. | |

It is certified that error appears in the above-identified patent and that said Letters Patent is hereby corrected as shown below:

Title page 1, (73) Assignee: "P)CIS, Inc." should read --PICIS, Inc.--.

Signed and Sealed this
Twenty-second Day of February, 2011

David J. Kappos
*Director of the United States Patent and Trademark Office*